United States Patent
Burckhardt et al.

(10) Patent No.: US 9,796,806 B2
(45) Date of Patent: Oct. 24, 2017

(54) DIOXOMOLYBDENUM (VI) COMPLEX COMPOUNDS AS CATALYSTS FOR POLYURETHANE COMPOSITIONS

(71) Applicant: SIKA TECHNOLOGY AG, Baar (CH)

(72) Inventors: Urs Burckhardt, Zurich (CH); Rita Cannas, Dubendorf (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

(21) Appl. No.: 15/214,861

(22) Filed: Jul. 20, 2016

(65) Prior Publication Data

US 2016/0326296 A1 Nov. 10, 2016

Related U.S. Application Data

(63) Continuation of application No. 14/358,925, filed as application No. PCT/EP2012/075202 on Dec. 12, 2012, now Pat. No. 9,422,390.

(30) Foreign Application Priority Data

Dec. 12, 2011 (EA) .................................. 11193060

(51) Int. Cl.

| | | |
|---|---|---|
| *C08F 8/00* | (2006.01) | |
| *C08G 63/91* | (2006.01) | |
| *C08G 77/00* | (2006.01) | |
| *C08G 77/38* | (2006.01) | |
| *C08L 63/00* | (2006.01) | |
| *C08G 59/14* | (2006.01) | |
| *C08G 18/22* | (2006.01) | |
| *C07F 11/00* | (2006.01) | |
| *C08G 18/48* | (2006.01) | |
| *C09D 175/08* | (2006.01) | |
| *C09J 175/08* | (2006.01) | |
| *C08G 18/76* | (2006.01) | |
| *C07C 235/80* | (2006.01) | |
| *C07D 295/108* | (2006.01) | |
| *C08G 18/12* | (2006.01) | |
| *C08K 5/56* | (2006.01) | |

(52) U.S. Cl.
CPC .......... *C08G 18/222* (2013.01); *C07C 235/80* (2013.01); *C07D 295/108* (2013.01); *C07F 11/005* (2013.01); *C08G 18/12* (2013.01); *C08G 18/4812* (2013.01); *C08G 18/4866* (2013.01); *C08G 18/7671* (2013.01); *C08K 5/56* (2013.01); *C09D 175/08* (2013.01); *C09J 175/08* (2013.01); *C08G 2190/00* (2013.01)

(58) Field of Classification Search
CPC .............. C08G 18/222; C08G 18/4866; C08G 18/4812; C08G 2190/00; C08G 18/7671; C08G 18/12; C07F 11/005; C09D 175/08; C09J 175/08; C07C 235/80; C07D 295/108; C08K 5/56
USPC .............. 525/52, 523, 55, 475, 474
See application file for complete search history.

(56) References Cited

U.S. PATENT DOCUMENTS

| | | |
|---|---|---|
| 2,916,464 A | 12/1959 | Ebneth et al. |
| 4,130,542 A | 12/1978 | Chang et al. |
| 4,256,627 A | 3/1981 | Moser et al. |
| 2003/0027969 A1 | 2/2003 | Ludewig et al. |

FOREIGN PATENT DOCUMENTS

| | | |
|---|---|---|
| DE | 10131463 A1 | 1/2003 |
| DE | 10308104 A1 | 9/2004 |
| DE | 10 2005 041 246 A1 | 3/2007 |
| WO | 2009/106722 A1 | 9/2009 |

OTHER PUBLICATIONS

Kenner et al., "Mo NMR Spectra if Dioxomolybdenum(VI) Complexes," Inorganica Chimica Acta, Jan. 1, 1981, pp. L27-L28, vol. 56, No. 2.
Abramenko et al., "Synthesis and IR Spectral Study of MoO2Cl2 Molecular Complexes with Acetoacetanilides. Crystal Structure of MoO2Cl2 Complex with Acetoacet-2-Toluidine," Russian Journal of Coordination Chemistry, 2000, pp. 866-871, vol. 26, No. 13.
International Search Report issued in International Application No. PCT/EP2012/075202 dated Apr. 2, 2013 (with translation).
International Preliminary Report on Patentability issued in International Patent Application No. PCT/EP2012/075202 dated Jun. 17, 2014.
Kenner A. Christensen et al., "95Mo NMR Spectra of Dioxomolybdenum (VI) Complexes," Inorganica Chimica Acta, 56 (1981), L27-L28.
Oct. 9, 2015 Office Action issued in Chinese Application No. 201280060955.5.
Jun. 12, 2016 Office Action issued in Chinese Application No. 201280060955.5.
Dec. 9, 2016 Office Action issued in Chinese Patent Application No. 201280060955.5.

*Primary Examiner* — David Karst

(74) *Attorney, Agent, or Firm* — Oliff PLC

(57) ABSTRACT

The invention relates to dioxomolybdenum (VI) complex compounds of the formula $MoO_2(L)_x(Y)_{2-x}$, where the ligand L has the formula (I). Such complex compounds are suitable in particular as catalysts for one- and two-component polyurethane compositions. The invention also relates to two-component polyurethane compositions including at least one polyisocyanate as the first component, at least one polyol as the second component, and at least one such dioxomolybdenum (VI) complex compound as the catalyst. The invention further relates to one-component polyurethane compositions comprising at least one polyurethane prepolymer with isocyanate groups, which are made from at least one polyisocyanate with at least one polyol, and comprising such a dioxomolybdenum (VI) complex compound as the catalyst. The invention additionally relates to different uses of said polyurethane compositions.

(I)

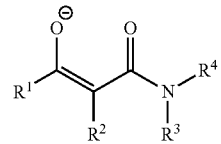

9 Claims, No Drawings

DIOXOMOLYBDENUM (VI) COMPLEX COMPOUNDS AS CATALYSTS FOR POLYURETHANE COMPOSITIONS

This is a Continuation of application Ser. No. 14/358,925 filed May 16, 2014, which is a National Stage Application of PCT/EP2012/075202 filed Dec. 12, 2013. The entire disclosures of the prior applications are hereby incorporated by reference herein their entirety.

DESCRIPTION

Technical Field

The present invention relates to the field of polyurethane compositions and of catalysts for polyurethane compositions.

Prior Art

Polyurethane compositions have been known for a long time and are used in numerous fields. Conventionally, a distinction is made in professional circles between single-component and two-component polyurethane compositions. Single-component polyurethane compositions cure under the influence of atmospheric moisture. Two-component polyurethane compositions contain a curing agent component as second component which contains substantially polyamines and/or polyols. In both cases, isocyanate group-containing compounds or prepolymers are used.

To accelerate the curing, catalysts are added. Although numerous polyurethane catalysts are known, most, however, are not particularly selective with regard to the urethanization reaction, i.e., the reaction of alcohol OH groups with isocyanate groups; instead they also catalyze to varying degrees other reactions of the isocyanate group, such as allophanate and biuret formation or cyclotrimerization. In particular, the urethanization reaction is usually in competition with the reaction of the isocyanate groups with water, which leads to urea groups with release of gaseous carbon dioxide. In the case of numerous polyurethane compositions, particularly if they are used as an adhesive or a sealant, as a coating or a casting resin, this side reaction has a disruptive effect, since, during the curing, it leads to bubble formation and thus to inferior dimensional stability, lower adhesive strength, lower mechanical strength, an unsatisfactory appearance and to poorly reproducible results. The water responsible for bubble formation originates either from the residual water content of the components of the composition, in particular of the polyols and of the fillers, which, even after drying processes, remain moist to varying degrees and have a typical residual water content of 0.01 to 0.5 wt %, or, from the ambient moisture which penetrates into the composition by diffusion from the air or from the substrates, which occurs particularly at high atmospheric humidity, in the case of porous substrates and/or hydrophilic polyols such as the polyether polyols frequently used in practice. The amine catalysts that are used in many cases in practice, for example, tertiary amines, and tin catalysts, for example, dialkyl tin carboxylates, are precisely the ones that frequently lead to pronounced bubble formation. The residual water content in the polyurethane composition moreover has the effect that hydrolysis sensitive catalysts, such as bismuth carboxylates, become deactivated, for example, if the composition is put aside for a longer duration before use (storage), which has a negative influence on the curing rate and on the mechanical properties. In the case of some known catalysts, for example, dialkyl tin carboxylates, the resistance of the cured composition is moreover insufficient under thermal stress, wherein the catalyst causes a lowering of the molecular weight, i.e., a depolymerization, with loss of mechanical strength. Furthermore, many of the known catalysts are solid at room temperature and sparsely soluble in the polyurethane starting materials or in plasticizers, so that, for their use in compositions that cure at room temperature, organic solvents have to be used. Finally, some of the known catalysts, particularly those based on heavy metal compounds, are toxicologically unsafe.

The use of dioxomolybdenum(VI) complexes as catalysts for curable compositions, for example, polyurethane compositions, is known. Thus, DE 101 31 463 A1 describes heat curable two-component coating systems the content of which includes dioxomolybdenum(VI) or dioxotungsten (VI) complexes of 1,3-diketone or 1,3-ketoester anions as ligands. Acetylacetonate is a preferred ligand. DE 103 08 104 discloses single-component polyurethane coating systems based on block diisocyanates, which contain, for example, dioxomolybdenum(VI) complexes of acetylacetonate or tetramethylheptane-3,5-dionate. WO 2009/106722 A1 discloses organopolysiloxanes that cure at room temperature and the content of which includes dioxomolybdenum(VI) complexes of 1,3-diketones. In contrast, according to DE 10 2005 041 246, the use of molybdenum or tungsten compounds is dispensed with, since they lead to interfering discolorations in the coatings. According to this disclosure, cesium compounds are used instead.

However, the known dioxomolybdenum(VI) complexes have a relatively poor thermal and hydrolytic stability and they hydrolyze gradually in a residual water-containing polyol, as a result of which the catalytic property cannot be preserved. Furthermore, their solubility in plasticizers or polyols is limited, and in systems that cure at room temperature they cannot be used without the use of volatile organic solvents (VOC).

Representation of the Invention

The problem of the present invention is to eliminate the above-described disadvantages of the prior art. In particular, the problem of the present invention is to provide a catalyst which leads to an improvement of the following properties or to a balanced ratio.

The catalyst should be characterized by high catalytic activity and selectivity with regard to the urethanization reaction, i.e., the reaction of alcohol OH groups with isocyanate groups, and thus it should make possible a rapid construction—disturbed as little as possible by moisture—of a mechanically high-quality polyurethane polymer from polyfunctional alcohols (polyols) and polyisocyanates. In addition, the catalyst should have a sufficient hydrolysis resistance in order to be preserved under the usual storage conditions, i.e., at room temperature or at slightly increased temperatures, for several months in a residual water-containing polyol composition without strong loss of activity. Moreover, the catalyst should lower the thermal resistance of the cured polyurethane polymer as little as possible. In addition, the catalyst should be liquid at room temperature or at slightly increased temperatures or it should be readily soluble in the polyurethane starting materials or in plasticizers, so that it can be used simply in solvent-free systems that cure at room temperature. Finally, the catalyst should have the lowest possible toxicity.

In particular, the catalyst should have good thermal and hydrolytic stability and it should not hydrolyze excessively rapidly in a residual water-containing polyol and thus preserve the catalytic activity, and it should also be liquid at room temperature and/or have a satisfactory solubility in plasticizers or polyols, in order to allow it thereby to be used simply in systems that cure at room temperature and without the use of volatile organic solvents (VOC).

Surprisingly, a novel dioxomolybdenum(VI) complex compound according to claim 1 having the desired properties has now been discovered. The dioxomolybdenum(VI) complex compound has formula $MoO_2(L)_x(Y)_{2-x}$, where x stands for 1 or 2, Y for a ligand with a single negative charge, and L for a ligand of the formula (I),

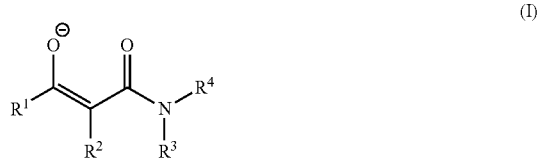

where $R^1$ and $R^2$, independently of one another, stand for a hydrogen residue, for a monovalent saturated or unsaturated hydrocarbon residue having 1 to 10 carbon atoms, or together stand for a bivalent alkylene residue having 3 to 6 carbon atoms, and $R^3$ and $R^4$, independently of one another, stand for a hydrogen residue, a monovalent saturated hydrocarbon residue, which optionally contains heteroatoms, having 1 to 12 carbon atoms, or together stand for a bivalent alkylene residue, which optionally contains heteroatoms, having 3 to 6 carbon atoms.

The ligand L of formula (I) formally has a single negative charge delocalized over the 1,3-ketoamide structure. Therefore, it can be drawn in the form of different resonance structures, for example, in the form of the resonance structures represented below. All the possible resonance structures of the ligands L of formula (I) are considered to be equivalent in the context of the present invention.

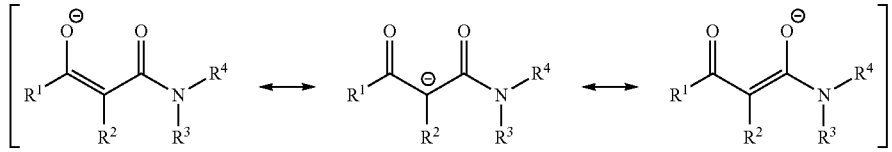

The ligand Y represents any ligand having a single negative charge, in particular a suitable organic anion, preferably a carbonylate, particularly preferably a 1,3-dicarbonylate, for example, acetylacetonate or 2,2,6,6-tetramethylheptane-3,5-dionate.

The dioxomolybdenum(VI) complex compound of formula $MoO_2(L)_x(Y)_{2-x}$ according to the invention with molybdenum as central atom and coordinatively bound ligands L and optionally Y is neutral and contains one or two ligands L of formula (I).

In the dioxomolybdenum(VI) complex compound of formula $MoO_2(L)_x(Y)_{2-x}$ according to the invention, x preferably stands for 2, since the complex compound of formula $MoO_2(L)_2$ is particularly stable. The two ligands L of formula (I) can here be identical or different. It is particularly preferable here to have two identical ligands L of formula (I).

In formula (I), $R^1$ and $R^2$ independently of one another stand for a hydrogen residue, for a monovalent saturated or unsaturated hydrocarbon residue having 1 to 10 carbon atoms, or together stand for a bivalent alkylene residue having 3 to 6 carbon atoms.

The monovalent saturated hydrocarbon residue having 1 to 10 carbon atoms is preferably an alkyl residue having 1 to 4 carbon atoms, in particular a methyl or a butyl residue. These have the advantage that the complex compound consequently tends to be liquid or readily soluble. The monovalent unsaturated hydrocarbon residue also preferably is an aryl residue, in particular a phenyl residue.

It is particularly preferable for $R^2$ to be a hydrogen residue, since the complex compound as a result tends to be particularly stable.

A bivalent alkylene residue having 3 to 6 carbon atoms is understood to be a residue of formula $—(CH_2)_n—$, where n stands for 3 to 6.

$R^1$ and $R^2$ together preferably form a bivalent alkylene residue having 3 to 4 carbon atoms, in particular 3 carbon atoms.

$R^3$ and $R^4$ independently of one another stand for a hydrogen residue, a monovalent saturated hydrocarbon residue, which optionally contains heteroatoms, having 1 to 12 carbon atoms, or together stand for a bivalent alkylene residue, which optionally contains heteroatoms, having 3 to 6 carbon atoms.

The monovalent saturated hydrocarbon residue having 1 to 12 carbon atoms is preferably an alkyl residue having 1 to 8 carbon atoms, particularly preferably a methyl, ethyl, propyl, isopropyl, butyl, isobutyl, hexyl, 2-methylpentyl, octyl- or 2-ethylhexyl residue. This has the advantage that the complex compound as a result tends to be liquid or readily soluble. The monovalent saturated hydrocarbon residue having 1 to 12 carbon atoms can preferably be a cycloalkyl residue having 5 to 6 carbon atoms, particularly preferably 6 carbon atoms. The monovalent saturated hydrocarbon residue with heteroatoms is preferably a hydroxyalkyl residue having 1 to 4 carbon atoms, particularly preferably a 2-hydroxyethyl or 2-hydroxypropyl residue. This has the advantage that the complex compound as a result tends to be liquid or readily soluble, and the ligand can be covalently integrated into the polymer during the curing. It is also preferable to use an alkyl ether residue having 1 to 4 carbon atoms, particularly preferably a 2-methoxyethyl or 2-(2-methoxy)ethoxyethyl residue, since the complex compound as a result tends to be liquid or readily soluble.

$R^3$ together with $R^4$ can also preferably form a bivalent alkylene residue of formula $—(CH_2)_n—X—(CH_2)_n—$ with X=O, NR, where R is a monovalent alkyl residue having 1 to 4 carbon atoms or S, and n=2 to 4. Particularly preferably n=2 and X=O or NR.

The selection of the preferred residue in the ligands L of formula (I) is preferably based on the fact that the corresponding 1,3-ketoamides, which are used as starting substances for preparing the dioxomolybdenum(VI) complex compound of formula $MoO_2(L)_x(Y)_{2-x}$ according to the invention, are easy to prepare and/or commercially available and consequently inexpensive.

It is preferable to use dioxomolybdenum(VI) complex compounds of formula $MoO_2(L)_2$ having two identical ligands L of formula (I), wherein $R^1$ stands for a methyl residue, $R^2$ stands for a hydrogen residue, and $R^3$ and $R^4$ respectively stand for an ethyl residue.

It is particularly preferable to use the following dioxomolybdenum(VI) complex compounds (1) to (8) of formula $MoO_2(L)_2$ having two identical ligands L of formula (I), where $R^1$ to $R^4$ have the meanings indicated in the table.

| | $R^1$ | $R^2$ | $R^3$ | $R^4$ |
|---|---|---|---|---|
| (1) | Alkyl residue having 1-4 carbon atoms | Hydrogen residue | Alkyl residue having 1-8 carbon atoms | Alkyl residue having 1-8 carbon atoms |
| (2) | Phenyl residue | Hydrogen residue | Alkyl residue having 1-8 carbon atoms | Alkyl residue having 1-8 carbon atoms |
| (3) | Alkyl residue having 1-4 carbon atoms | Hydrogen residue | Alkyl ether residue having 1-4 carbon atoms | Alkyl ether residue having 1-4 carbon atoms |
| (4) | | Alkylene residue having 3-6 carbon atoms | | Alkyl residue having 1-8 carbon atoms |
| (5) | Alkyl residue having 1-4 carbon atoms | Hydrogen residue | | Alkylene residue of formula $-(CH_2)_n-X-(CH_2)_n-$ with X = O or NR and n = 2 |
| (6) | Alkyl residue having 1-4 carbon atoms, | Hydrogen residue | Cycloalkyl residue having 5-6 carbon atoms | Alkyl residue having 1-8 carbon atoms |
| (7) | Alkyl residue having 1-4 carbon atoms | Hydrogen residue | Alkyl residue having 1-8 carbon atoms | Cycloalkyl residue having 5-6 carbon atoms |
| (8) | Phenyl residue | Hydrogen residue | | Alkylene residue of formula $(-CH_2)_n-X-(CH_2)_n-$ with X = O or NR and n = 2 |

In a preferred embodiment, the dioxomolybdenum(VI) complex compounds of formula $MoO_2(L)_x(Y)_{2-x}$ according to the invention are not dioxomolybdenum(VI) bis(N,N-diethyl-3-oxobutane amidate).

The preparation of the dioxomolybdenum(VI) complex compound of formula $MoO_2(L)_x(Y)_{2-x}$ according to the invention occurs by reacting a 1,3-ketoamide of formula

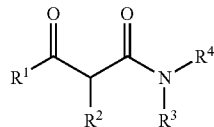

with $R^1$, $R^2$, $R^3$, and $R^4$, as defined above, with a dioxomolybdenum(VI) salt or complex. It is preferable to use molybdate alkali metal salts, such as sodium molybdate dihydrate, and dioxomolybdenum(VI) bis(acetylacetonate).

The 1,3-ketoamide here can be used in stoichiometric or above stoichiometric quantities. In the case of an above stoichiometric use of 1,3-ketoamide, the dioxomolybdenum(VI) complex compound according to the invention tends to have an increased hydrolysis stability and a lower viscosity. It is preferable for the stoichiometric ratio between the dioxomolybdenum(VI) salt or complex and the 1,3-ketoamide to be in the range from 1:2 to 1:4.

The preferably dried dioxomolybdenum(VI) salt or complex is mixed with the 1,3-ketoamide, and the mixture is heated preferably under stirring for 1 to 24 hours, preferably for approximately 2 hours, at a temperature of 50 to 130° C., in particularly of approximately 80° C. Subsequently, volatile components are removed from the reaction mixture preferably in a vacuum. The dioxomolybdenum(VI) salt or complex can also be dissolved in hydrochloric acid, followed by admixing the 1,3-ketoamide, and the mixture can be stirred for 10 to 25 hours, preferably for approximately 18 hours, at approximately room temperature. Furthermore, the 1,3-ketoamide can also be used dissolved in an organic solvent, preferably a high boiling point organic solvent, in particular tetraethylene glycol dimethyl ether (TEGDME).

The dioxomolybdenum(VI) complex compound according to the invention can be used as a catalyst for curable compositions, preferably for polyurethane compositions. The dioxomolybdenum(VI) complex compound according to the invention accelerates the curing of curable compositions, which comprise reactive groups capable of undergoing crosslinking reactions. The curable compositions can be formulated to be single-component or multi-compositions.

It is preferable for the dioxomolybdenum(VI) complex compound to accelerate the curing of two-component polyurethane compositions, which crosslink with themselves or if applicable under the influence of moisture via blocked or in particular free isocyanate groups. In the process, the urethanization reaction, i.e., the reaction of isocyanate groups with alcohol OH groups, is accelerated above all. The compositions to be crosslinked can also contain additional reactive groups that are capable of undergoing crosslinking reactions, such as alkoxysilane groups, in particular. Said groups are preferably trialkoxysilane groups as contained in silane adhesive promoters, for example.

The dioxomolybdenum(VI) complex compound according to the invention can be used advantageously as a catalyst in a two-component polyurethane composition. This composition comprises, in addition to the dioxomolybdenum(VI) complex compound according to the invention, a polyol as first component as well as a polyisocyanate as second component.

The term "two-component" denotes a composition in which the constituents thereof are in the form of two different components, which are stored in containers that are separate from one another and that are each individually storage-stable. It is only shortly before or during the application of the composition that the two components are mixed with one another, after which the mixed composition is cured, wherein the curing under some circumstances occurs or is completed only due to the influence of moisture and/or increased temperature.

Substance names, such as polyol or polyisocyanate, that start with "poly" denote substances that formally contain two or more of the functional groups that occur in their name per molecule.

The term "polyisocyanate" comprises compounds with two or more isocyanate groups, independently of whether they are polymers that comprise monomeric diisocyanates, oligomeric polyisocyanates or isocyanate groups.

A suitable polyisocyanate is, for example, a polyisocyanate in the form of a monomeric diisocyanate or triisocyanate or of an oligomer of a monomeric diisocyanate or of a derivative of a monomeric diisocyanate.

Suitable monomeric diisocyanates or triisocyanates are, for example, 1,4-tetramethylene diisocyanate, 2-methylpentamethylene-1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane-1,3- and -1,4-diisocyanate, 1-methyl-2,4- and -2,6-diisocyanatocyclohexane and any desired mixtures of these isomers, 1-isocyanato-3,3,5-trimethyl-5-isocyanatomethyl-cyclohexane (=isophorone diisocyanate or IPDI), perhydro-2,4'- and -4,4'-diphenylmethane diisocyanate (HMDI), 1,4-diisocyanato-2,2,6-trimethylcyclohexane (TMCDI), 1,3- and 1,4-bis-(isocyanatomethyl) cyclohexane, m- and p-xylylene diisocyanate (m- and p-XDI), m- and p-tetramethyl-1,3- and -1,4-xylylene diisocyanate (m- and p-TMXDI), bis-(1-isocyanato-1-methylethyl)naphthalene, dimer and trimer fatty acid isocyanates, such as 3,6-bis-(9-isocyanatononyl)-4,5-di-(1-heptenyl)cyclohexene (dimeryl diisocyanate), α,α,α',α'',α''-hexamethyl-1,3,5-mesitylene triisocyanate, 2,4- and 2,6-toluylene diisocyanate and any mixtures of these isomers (TDI), 4,4'-, 2,4'- and 2,2'-diphenylmethane diisocyanate and any mixtures of these isomers (MDI), mixtures of MDI and MDI homologs (polymer MDI or PMDI), 1,3- and 1,4-phenylene diisocyanate, 2,3,5,6-tetramethyl-1,4-diisocyanatobenzene, 1,5-naphthalene diisocyanate (NDI), 3,3'-dimethyl-4,4'-diisocyanatodiphenyl (TODI), dianisidine diisocyanate (DADI), 1,3,5-tris-(isocyanatomethyl)benzene, tris-(4-isocyanatophenyl)methane, and tris-(4-isocyanatophenyl)thiophosphate.

Preferred polyisocyanates are commercial diisocyanates. It is particularly preferable to use HDI, IPDI, TDI and MDI as well as oligomers of polyurethane polymers that contain diisocyanates and isocyanate, (NCO prepolymers).

As polyols one can use, for example, the following commercial polyols or mixtures thereof:

Polyoxyalkylene polyols, also referred to as polyether polyols or oligoetherols, which are polymerization products of ethylene oxide, 1,2-propylene oxide, 1,2- or 2,3-butylene oxide, oxetane, tetrahydrofuran or mixtures thereof, optionally polymerized using a starter molecule with two or more active hydrogen atoms, such as, for example, water, ammonia or compounds with several OH or NH groups, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexane dimethanol, bisphenol A, hydrogenated bisphenol A, 1,1,1-trimethylolethane, 1,1,1-trimethylolpropane, glycerol, aniline as well as mixtures of the above-mentioned compounds. It is also possible to use both polyoxyalkylene polyols having a low degree of unsaturation (measured according to ASTM D-2849-69 and indicated in milliequivalent unsaturation per gram polyol (mEq/g)), prepared, for example, using the so-called Double Metal Cyanide Complex catalysts (DMC catalysts) and also polyoxyalkylene polyols having a higher degree of unsaturation, produced, for example, using anionic catalysts, such as, NaOH, KOH, CsOH or alkali alcoholates.

Particularly suitable are polyoxyalkylenediols or polyoxyalkylenetriols, in particular polyoxyethylene- and polyoxypropylenediols and -triols. Especially suitable are polyoxyalkylenediols and -triols having a degree of unsaturation of less than 0.02 mEq/g and a molecular weight in the range of 1000-30,000 g/mol, as well as polyoxypropylenediols and -triols having a molecular weight of 400-8000 g/mol.

Also particularly suitable are so-called ethylene oxide-terminated ("EO-endcapped," ethylene oxide-endcapped) polyoxypropylene polyols. The latter are special polyoxypropylene polyoxyethylene polyols prepared, for example, by further alkoxylating pure polyoxypropylene polyols, in particular polyoxypropylenediols and -triols, with ethylene oxide after the completion of the polypropoxylation reaction, which as a result have primary hydroxyl groups.

Styrene acrylonitrile or acrylonitrile methyl methacrylate-grafted polyether polyols.

Polyester polyols, also referred to as oligoesterols, prepared by known methods, in particular by the polycondensation of hydroxycarboxylic acids or the polycondensation of aliphatic and/or aromatic polycarboxylic acids with bivalent or polyvalent alcohols.

Particularly suitable polyester polyols are those that are prepared from bivalent to trivalent alcohols, in particular bivalent alcohols, such as, for example, ethylene glycol, diethylene glycol, propylene glycol, dipropylene glycol, neopentyl glycol, 1,4-butanediol, 1,5-pentanediol, 3-methyl-1,5-hexanediol, 1,6-hexanediol, 1,8-octanediol, 1,10-decanediol, 1,12-dodecanediol, 1,12-hydroxystearyl alcohol, 1,4-cyclohexanedimethanol, dimer fatty acid diol (dimerdiol), hydroxypivalic acid neopentyl glycol ester, glycerol, 1,1,1-trimethylolpropane or mixtures of the above-mentioned alcohols, with organic dicarboxylic or tricarboxylic acids, in particular dicarboxylic acids, or their anhydrides or esters, such as, for example, succinic acid, glutaric acid, adipic acid, trimethyl adipic acid, suberic acid, azelaic acid, sebacic acid, dodecanedicarboxylic acid, maleic acid, fumaric acid, dimer fatty acid, phthalic acid, phthalic acid anhydride, isophthalic acid, terephthalic acid, dimethyl terephthalate, hexahydrophthalic acid, trimellitic acid and trimellitic acid anhydride, or mixtures of the above-mentioned acids, as well as polyester polyols from lactones, such as, for example, from ε-caprolactone, and starters such as the above-mentioned bivalent or trivalent alcohols.

Polycarbonate polyols, as produced by reacting, for example, the above-mentioned alcohols—used for the construction of the polyester polyols—with dialkyl carbonates, diaryl carbonates or phosgene.

Block copolymers bearing at least two hydroxyl groups, which have at least two different blocks with polyether, polyester and/or polycarbonate structure of the above-described type, in particular polyether polyester polyols.

Polyacrylate and polymethacrylate polyols.

Polyhydroxy-functional fats and oils, for example, natural fats and oils, particularly castor oil; or so-called oleochemical polyols—prepared by chemical modification of natural fats and oils —, for example, the epoxy polyesters or epoxy polyethers obtained by epoxidation of unsaturated oils followed by ring opening with carboxylic acids or alcohols, or the polyols obtained by hydroformylation and hydrogenation of unsaturated oils; or polyols obtained from natural fats and oils by degradation processes, such as alcoholysis or ozonolysis and subsequent chemical linking, for example, by transesterification or dimerization, of the resulting degradation products or derivatives thereof. Suitable degradation products of natural fats and oils are, in particular, fatty acids and fatty alcohols as well as fatty acid esters, in particular methyl esters (FAME), which can be derivatized, for example, by hydroformylation and hydrogenation to form hydroxy fatty acid esters.

Polyhydrocarbon polyols, also referred to as oligo hydrocarbonols, such as, for example, polyhydroxy functional polyolefins, polyisobutylenes, polyisoprenes; polyhydroxy functional ethylene-propylene, ethylene-butylene or ethylene-propylene-diene copolymers; polyhydroxy functional polymers of dienes, in particular of 1,3-butadiene, which can in particular also be produced by anionic polymerization; polyhydroxy functional copolymers of dienes, such as 1,3-butadiene or diene mixtures, and vinyl monomers, such as styrene, acrylonitrile, vinyl chloride, vinyl acetate, vinyl alcohol, isobutylene and isoprene, for example, polyhydroxy functional acrylonitrile/butadiene copolymers, as can be produced, for example, from epoxides or amino alcohols and carboxyl-terminated acrylonitrile/butadiene copolymers; as well as hydrogenated polyhydroxy functional polymers or copolymers of dienes.

The mentioned polyols preferably have an average molecular weight of 250-30,000 g/mol, in particular of 400-20,000 g/mol, and furthermore they preferably have an average OH functionality in the range from 1.6 to 3.

The term "molecular weight" in the case of oligomers or polymers always refers to the average molecular weight $M_n$.

It is particularly preferable to use polyether polyols, preferably polypropylene polyols and polyethylene-polypropylene mixed polyols, as well as polyester polyols and polycarbonate polyols.

The dioxomolybdenum(VI) complex compound according to the invention is preferably located in the first component, which has the advantage that the storage stability (shelf life) of the polyisocyanate, which is sensitive to catalytically acting compounds, is not affected in the second component.

The dioxomolybdenum(VI) complex compound according to the invention can be used as the sole catalyst, or also together with other catalysts, such as, for example, bismuth, tin or zirconium compounds, or tertiary amines.

The two-component polyurethane composition according to the invention can optionally contain additional typically used auxiliary substances and additives, for example, pigments, plasticizers or diluents, curing agents, crosslinking agents, chain elongation agents, additional catalysts, adhesive promoters, stabilizers, rheological aids and desiccants, etc.

The dioxomolybdenum(VI) complex compound according to the invention, in terms of quantity of elemental molybdenum, is preferably present in the two-component polyurethane composition according to the invention in a quantity of 0.002 to 1 wt %, particularly preferably in a quantity of 0.01 to 0.5 wt %, and quite particularly preferably in a quantity of 0.02 to 0.3 wt %, relative to the weight of the composition. Excessively large quantities lead to too short an open time or processing time of the composition, whereas the use of smaller quantities has the disadvantage that the composition is catalyzed too weakly and it thus cures too slowly, incompletely and/or defectively. In the two-component polyurethane composition according to the invention, the dioxomolybdenum(VI) complex compound according to the invention represents preferably 0.02 to 10, preferably 0.1 to 5, particularly preferably 0.2 to 3 mmol equivalents of molybdenum atoms per 100 g of the composition.

As already mentioned above, with regard to the urethanization reaction, the dioxomolybdenum(VI) complex compound according to the invention is relatively active and also relatively selective. In comparison to dioxomolybdenum (VI) bis(acetylacetonate) and also in comparison to molybdenum carboxylate, the dioxomolybdenum(VI) complex compound according to the invention is characterized by a clearly higher catalytic activity. In general, the curing of the two-component polyurethane composition according to the invention occurs rapidly. However, the selectivity of the dioxomolybdenum(VI) complex compound according to the invention does not suffer due to the increased activity; the curing occurs without formation of bubbles, even under disadvantageous conditions, such as high temperature, high ambient moisture and a high residual water content of the compound as well as in the case of the use of polyols with secondary OH or hydrophilic groups. The dioxomolybdenum(VI) complex compound according to the invention is relatively stable thermally and hydrolytically and even in a polyol containing residual water it decomposes only slowly and thus keeps its catalytic activity even in the case of a longer storage time. The use of the dioxomolybdenum(VI) complex compound according to the invention still leads to a satisfactory stability of the cured polyurethane composition even under thermal exposure. Furthermore, the dioxomolybdenum(VI) complex compound according to the invention is liquid at room temperature and/or readily soluble in plasticizers or polyols, and it can be used simply in systems that cure at room temperature, and in particular without the use of volatile organic solvents (VOC). Finally, the dioxomolybdenum(VI) complex compound according to the invention is only slightly colored and it leads to hardly any discoloration of the cured polyurethane composition; it also has a relatively low toxicity.

The two-component polyurethane composition according to the invention can be used in numerous fields, for example, as a casting composition, sealant, adhesive, covering, coating, paint, primer, hard foam, soft foam, molded part, elastomer, fiber, film or membrane for applications in construction and industry, for example, as an electro casting composition, spackling compound, seam sealant, cavity sealant, joint sealant, assembly adhesive, car body adhesive, plate adhesive, sandwich element adhesive, laminating adhesive, laminate adhesive, packaging adhesive, wood adhesive, parquet adhesive, anchoring adhesive, bottom covering and coating, balcony and roof coating, concrete protection coating, parking garage coating, pipe coating, corrosion protection coating, textile coating, wood paint, decoration paint, primer, furniture foam, padding foam, filter foam, insulation foam, sound insulation foam, sealing foam, packaging foam, car body foam, model building plate, damping element, sealing element, tires, rolls, bearings, rollers, conveyor belt, elastic threads, shoe soles, casings, window profile section, implant, foam rubber, etc.

Preferred application fields are casting compositions, sealants, adhesives, coverings, coatings, paints, primers, molded parts and elastomers for applications in construction and industry, The dioxomolybdenum(VI) complex compound according to the invention can also be used in single-component polyurethane compositions. These compositions comprise, in addition to the dioxomolybdenum(VI) complex compound according to the invention, at least one polyurethane prepolymer with isocyanate terminal groups, which is prepared from at least one polyisocyanate and at least one polyol. The polyurethane prepolymer is prepared in the usual manner, for example, as described in EP 1 408 062 A1. The polyols used for the prepolymer preparation are polyols as described in EP 1 408 062 and in the above. The same applies to the polyisocyanates used for preparing the polyurethane prepolymers.

In the single-component polyurethane composition according to the invention, the dioxomolybdenum(VI) complex compound according to the invention represents 0.01 to 10, preferably 0.05 to 2, and particularly preferably 0.1 to 1 mmol equivalents of molybdenum atoms per 100 g of the composition.

Single-component polyurethane compositions containing a dioxomolybdenum(VI) complex compound according to the invention typically have a comparatively satisfactory storage stability as well as a comparatively short skin formation time.

The fields of application of the single-component polyurethane composition according to the invention correspond to those mentioned above in connection with the applications of the two-component polyurethane compositions.

The dioxomolybdenum(VI) complex compound according to the invention has a satisfactory thermal and also hydrolytic stability. Therefore, it does not hydrolyze rapidly in a residual water-containing polyol and thus preserves its catalytic activity. Furthermore, it is liquid at room temperature and/or has a satisfactory solubility in plasticizers or polyols. As a result, its use in systems that cure at room temperature is simple and does not require the use of volatile organic solvents (VOC). The catalytic activity and selectivity of the dioxomolybdenum(VI) complex compound according to the invention is excellent with regard to the urethanization reaction. Single-component and two-component polyurethane compositions cured with the complex compound according to the invention are characterized by a satisfactory thermal resistance, in spite of the hydrolysis stability of the complex compound.

In addition to its use in single-component and two-component polyurethane compositions, the dioxomolybdenum(VI) complex compound according to the invention can also be used as catalyst or cocatalyst in other curable compositions, for example, in epoxy resins, acrylates, and silicones.

EXAMPLES

Description of the Measurement Methods

The infrared spectra were measured with a Perkin-Elmer 1600 FT-IR apparatus (horizontal ATR measurement unit with ZnSe crystals; measurement window 4000-650 $cm^{-1}$). Undiluted liquid samples were applied as films, and solid samples were dissolved in $CH_2Cl_2$. The absorption bands are indicated using wave numbers ($cm^{-1}$).

The $^1$H-NMR spectra were measured on a Bruker DPX-300 spectrometer at 300.13 MHz; the chemical δ shifts are indicated in ppm relative to tetramethylsilane (TMS). No distinction was made between true and pseudo coupling patterns.

The viscosity was measured with a thermostated Physica MCR 300 cone-plate viscometer (cone diameter 20 mm, cone angle 1°, cone tip-plate distance 0.05 mm, shear rate 0.1 to 100 $s^{-1}$).

The UV-vis spectra of samples (40 mg/L) dissolved in dichloromethane were measured in 1 cm quartz cuvettes with a Varian Cary 50 spectrometer in the wavelength range 800-200 nm. The extinction maxima $δ_{max}$ are indicated in nm, and the associated extinction coefficients ϵ are given in $l·g^{-1}·cm^{-1}$ in parentheses.

Preparation of the Dioxomolybdenum(VI) Complex Compounds

General Preparation Procedure A

In a round-bottom flask, dried dioxomolybdenum(VI) bis(acetylacetonate) and a 1,3-ketoamide were mixed, and the mixture was heated under stirring for 2 hours at 80° C. Subsequently, the volatile components were removed from the reaction mixture in a vacuum.

General Preparation Procedure B

In a round-bottom flask, sodium molybdate dihydrate ($Na_2MoO_4.2H_2O$) was mixed in 15 mL hydrochloric acid solution (0.1 M). A 1,3-ketoamide was mixed into this solution, and the mixture was stirred for 18 hours at 23° C. Subsequently the reaction mixture was filtered and the resulting solid was dried in a vacuum.

General Preparation Procedure C

In a round-bottom flask, a mixture of dried dioxomolybdenum(VI) bis(acetylacetonate) and a 1,3-ketoamide in tetraethylene glycol dimethyl ether (TEGDME) was heated under stirring for 3 hours at 80° C. Subsequently, the reaction mixture was cooled to room temperature.

Example 1

Dioxomolybdenum(VI) Bis(N,N-Diethyl-3-Oxobutane Amidate)

3.26 g Dioxomolybdenum(VI) bis(acetylacetonate) and 3.33 g N,N-diethyl-3-oxobutane amide were reacted according to General Preparation Procedure A. The product consisted of 4.49 g of a yellow, microcrystalline solid.

$^1$H-NMR(CDCl$_3$):δ1.5 and 1.9(2×t,12H,CH$_3$CH$_2$),2.0(s, 6H,CH$_3$CO),3.15,3.3 and 3.55(3×dq,8H,CH$_3$CH$_2$),5.2(s,2H, enol-CH).

FT-IR:2974,2932,2872,1720,1594,1491,1437,1358,1308, 1276,1197,1081,1015, 961,929,903,773,660.

UV-vis: 309(0.11) and 275(0.23). (compare dioxomolybdenum(VI) bis(acetylacetonate):314(0.13) and 270(0.27).)

Example 2

Dioxomolybdenum(VI) Bis(n,n-Diethyl-3-Oxobutane Amidate) in TEGDME 6.54 g Dioxomolybdenum(VI) bis(acetylacetonate) and 7.21 g N,N-diethyl-3-oxobutane amide were reacted in 18.00 g TEGDME according to General Preparation Procedure C. The product consisted of 31.75 g of an orange-colored solution.

Example 3

Dioxomolybdenum(VI)
Bis(N,N-Dibutyl-3-Oxobutane Amidate)

3.26 g Dioxomolybdenum(VI) bis(acetylacetonate) and 4.48 g N,N-dibutyl-3-oxobutane amide were reacted according to General Preparation Procedure A. The product consisted of 6.12 g of a yellow solid.
$^1$H-NMR(CDCl$_3$):δ0.9(dt, 12H,Me),1.2-1.5(m,8H, CH$_2$Me),1.5-1.6(m,8H, CH$_2$CH$_2$N),2.0(s,6H,MeCO),2.9-3.0(m,4H,NCH$_2$),3.1-3.3(m,8H,NCH$_2$),3.5-3.65(m, 4H,NCH$_2$),5.15(s,2H,enol-CH).
FT-IR:3500,2916,2854,1717,1582,1505,1445,1361,1255, 1192,1112,987,958, 904,860,771,731,670.

Example 4

Dioxomolybdenum(VI)
Bis(N,N-Bis(2-Methoxyethyl)-3-Oxobutane Amidate)

3.26 g Dioxomolybdenum(VI) bis(acetylacetonate) and 4.56 g N,N-bis(2-methoxyethyl)-3-oxobutane amide were reacted according to General Preparation Procedure A. The product consisted of 6.15 g of a brownish, highly viscous oil.
$^1$H-NMR(CDCl$_3$):δ1.95,2.0,2.05,2.15(4×s,6H,MeCO), 3.35 (s,12H,OMe),3.4-3.8(m,16H,NCH$_2$and OCH$_2$),5.3,5.4, 5.5and 5.7(4×s,2H,enol-CH)
FT-IR:2925,2889,1718,1636,1587,1501,1430,1355,1274, 1191,1110,1007,960, 927, 898, 774, 662.

Example 5

Dioxomolybdenum(VI)
Bis(N,N-Bis(2-Methoxyethyl)-3-Oxobutane Amidate) in TEGDME 3.26 g Dioxomolybdenum(VI) bis(acetylacetonate) and 4.79 g N,N-bis(2-methoxyethyl)-3-oxobutane amide were reacted in 9.16 g TEGDME according to General Preparation Procedure C. The product consisted of 17.21 g of an orange-colored solution.

Example 6

Dioxomolybdenum(VI)
Bis(N-Cyclohexyl-N-Methyl-3-Oxobutane Amidate)

3.26 g Dioxomolybdenum(VI) bis(acetylacetonate) and 4.14 g N-cyclohexyl-N-methyl-3-oxobutane amide were reacted according to General Preparation Procedure A. The product consisted of 5.94 g of an orange-colored, highly viscous oil.
$^1$H-NMR(CDCl$_3$):δ1.0-1.9(m, 20H,CH$_2$),2.0-2.1 (m,6H, MeCO),2.3(s,3H,Me from the ligand),2.75-2.9(4×s,6H, NMe),4.2-4.5(m,2H, CHN),5.15-5.6(8×s,2H,enol-CH).
FT-IR:2926,2854,1719,1601,1508,1449,1346,1316,1265, 1199,1164,1010,956, 932,902,773,731,701.

Example 7

Dioxomolybdenum(VI)
Bis(N-Cyclohexyl-N-Methyl-3-Oxobutane Amidate) in TEGDME 3.31 g Dioxomolybdenum(VI) bis(acetylacetonate) and 4.49 g N-cyclohexyl-N-methyl-3-oxobutane amide were reacted in 10.50 g TEGDME according to General Preparation Procedure C. The product consisted of 18.30 g of an orange-colored solution.

Example 8

Dioxomolybdenum(VI)
Bis(1-Morpholinobutane-1,3-Dionate)

3.26 g Dioxomolybdenum(VI) bis(acetylacetonate) and 3.59 g 1-morpholinobutane-1,3-dione were reacted according to General Preparation Procedure A. The product consisted of 5.41 g of a yellow solid.
$^1$H-NMR(CDCl$_3$):δ2.05(s,3H,MeCO),3.4-3.8(m,16H, NCH$_2$and OCH$_2$),5.25(s,2H, enol-CH).
FT-IR:2955,2870,1734,1606,1505,1464,1433,1366,1293, 1228,1193,955,931, 901,772,734,697.

Example 9

Dioxomolybdenum(VI) Bis(1-(4-Methylpiperazin-1-Yl)Butane-1,3-Dionate)

3.26 g Dioxomolybdenum(VI) bis(acetylacetonate) and 3.87 g 1-(4-methylpiperazin-1-yl)butane-1,3-dione were reacted according to General Preparation Procedure A. The product consisted of 6.02 g of an orange-colored, highly viscous oil. $^1$H-NMR(CDCl$_3$):δ2.05(s,6H,MeCO),2.3(d, 6H,NMe),2.4(dd,8H,NCH$_2$),3.45 (dd,4H,CH$_2$N),3.65(dd, 2H,CH$_2$N),5.15,5.25,5.5(3×s, 2H,enol-CH).
FT-IR:3411,2938,2791,1719,1606,1499,1446,1360,1291, 1260,1142,991,959, 930,903,772,669.

Example 10

Dioxomolybdenum(VI)
Bis(N,N-Dibutyl-3-Oxoheptane Amidate)

3.19 g Dioxomolybdenum(VI) bis(acetylacetonate) and 5.26 g N,N-dibutyl-3-oxoheptane amide were reacted according to General Preparation Procedure A. The product consisted of 6.52 g of an orange-yellow, highly viscous oil.
$^1$H-NMR (CDCl$_3$):δ0.85-1.0(m, 18H,Me),1.3-1.45(m, 12H,CH$_2$Me),1.5-1.65(m, 12H,CH$_2$CH$_2$Me),2.05-2.3(m, 4H,CH$_2$CO),2.9-3.0 (m,2H,CH$_2$N),3.15-3.45(m,6H, CH$_2$N),3.5-3.65(br s,2H, remaining CH$_2$),5.15,5.25and 5.7 (3×s,2H,enol-CH).
FT-IR:2954,2870,1737,1604,1584,1501,1463,1369,1292, 1226,1185,930,902, 774,733.

Example 11

Dioxomolybdenum(VI)
Bis(N,N-Dibutyl-3-Oxoheptane Amidate) in TEGDME 3.24 g Dioxomolybdenum(VI) bis(acetylacetonate) and 5.58 g N,N-dibutyl-3-oxoheptane amide were reacted in 6.70 g TEGDME according to General Preparation Procedure C. The product consisted of 15.52 g of an orange-colored solution.

Example 12

Dioxomolybdenum(VI)
Bis(N,N-Bis(2-Methoxyethyl)-3-Oxoheptane Amidate)

3.72 g Dioxomolybdenum(VI) bis(acetylacetonate) and 6.21 g N,N-bis(2-methoxyethyl)-3-oxoheptane amide were reacted according to General Preparation Procedure A. The product consisted of 7.66 g of an orange-yellow solid.

$^1$H-NMR(CDCl$_3$):δ0.9(t, 6H,Me),1.35(dq,4H,CH$_2$Me), 1.5-1.7 (m,4H, CH$_2$CH$_2$Me),2.25(t,4H,CH$_2$CO),3.35(s, 12H,OMe),3.3-3.8(m,20H,CH$_2$O,CH$_2$N and CH$_2$),5.3(s,2H, enol-CH).

FT-IR:2927,2871,1746,1716,1602,1502,1372,1274,1185, 1115,1012,957,927, 904,775.

Example 13

Dioxomolybdenum(VI) Bis(N-Cyclohexyl-N-Methyl-3-Oxoheptane Amidate)

3.66 g Dioxomolybdenum(VI) bis(acetylacetonate) and 5.03 g N-cyclohexyl-N-methyl-3-oxoheptane amide were reacted according to General Preparation Procedure A. The product consisted of 6.86 g of a brownish, highly viscous oil.

$^1$H-NMR(DMSO-d$_6$):δ0.7-0.9(m,6H,Me),1.0-1.9(m, 28H,CH$_2$Me,CH$_2$CH$_2$Me, CH$_2$),2.2-2.3(m,4H,CH$_2$CO), 2.7-2.9(m,6H,NMe),4.2-4.3(m,2H,CHN),5.4,5.5,5.7, 5.9(4×s,2H,enol-CH).

FT-IR:2926,2855,1739,1717,1601,1498,1449,1350,1318, 1254,1189,1164,1025, 970,930,900,774,729,667.

Example 14

Dioxomolybdenum(VI) Bis(1-Morpholinoheptane-1,3-Dionate)

3.66 g Dioxomolybdenum(VI) bis(acetylacetonate) and 5.03 g 1-morpholinoheptane-1,3-dione were reacted according to General Preparation Procedure A. The product consisted of 6.58 g of a brownish, highly viscous oil.

$^1$H-NMR(DMSO-d$_6$):δ0.8-0.9(m,6H,Me),1.2-1.35(m, 4H,CH$_2$Me),1.4-1.5(m,4H,CH$_2$CH$_2$Me),3.3-3.7 (m, 16H, CH$_2$O,CH$_2$N and CH$_2$),5.55,5.65,5.95(3×s,2H,enol-CH).

FT-IR:2956,2857,1717,1600,1500,1441,1370,1251,1185, 1113,929,900,861,772, 667.

Example 15

Dioxomolybdenum(VI) Bis(N,N-Diethyl-3-Phenyl-3-Oxopropane Amidate)

2.05 g sodium molybdate dihydrate and 4.33 g N,N-diethyl-3-phenyl-3-oxopropanamide were reacted according to General Preparation Procedure B. The product consisted of 5.18 g of a yellow, microcrystalline solid.

$^1$H-NMR(DMSO-d$_6$):δ0.9and 1.15(2×t,12H,Me),3.1-3.6 (m, 8H,CH$_2$Me),6.1(s,2H,enol-CH),7.45-7.5(m,6H,arom-H),7.8-7.85(m, 4H,arom-H).

FT-IR:2975,1605,1573,488,1439,1357,1282,1238,1101, 929,899,765,694,673.

Example 16

Dioxomolybdenum(VI) Bis(N,N-Dibutyl-3-Oxo-3-Phenyl Propane Amidate)

3.26 g Dioxomolybdenum(VI) bis(acetylacetonate) and 5.78 g N,N-dibutyl-3-oxo-3-phenyl propanamide were reacted according to General Preparation Procedure A. The product consisted of 7.35 g of a yellow solid.

$^1$H-NMR(CDCl$_3$):δ0.7(t,12H,Me),0.9-1.0(m,12H, Me), 1.3-1.45(m,8H, CH$_2$Me),1.5-1.7(m,8H,CH$_2$CH2Me),2.9-3.05(m,2H,CH$_2$N),3.2-3.4(m,2H,CH$_2$N), 3.45-3.6(m,2H, CH$_2$N),5.7,5.9,5.95(4×s,2H,enol-CH), 7.35-7.45(m, 6H,arom-H),7.75-7.8 (m, 4H, arom-H).

FT-IR: 2955,2869,1740,1684,1604,1572,1488,1358, 1294,1215,1104,1022,932, 901,765,734,692.

Example 17

Dioxomolybdenum(VI) Bis(N,N-Dibutyl-3-Oxo-3-Phenyl Propanamidate) in TEGDME 3.37 g Dioxomolybdenum(VI) bis(acetylacetonate) and 6.25 g N,N-dibutyl-3-oxo-3-phenyl propanamide were reacted in 6.76 g TEGDME according to General Preparation Procedure C. The product consisted of 16.38 g of a yellow orange solution.

Example 18

Dioxomolybdenum(VI) Bis(1-Morpholino-3-Phenylpropane-1,3-Dionate)

3.26 g Dioxomolybdenum(VI) bis(acetylacetonate) and 4.90 g 1-morpholino-3-phenylpropane-1,3-dione were reacted according to General Preparation Procedure A. The product consisted of 7.09 g of an orange-yellow solid.

$^1$H-NMR(CDCl$_3$):δ3.4-3.85(m, 16H,CH$_2$N and CH$_2$O), 5.5,5.75,5.8,5.9and 5.05(5×s,2H,enol-CH),7.35-7.5(m,6H, arom-H),7.75-7.85(m, 2H,arom-H),8.0-8.1(m,2H, arom-H).

FT-IR:3056,2967,2918,2856,2359,1684,1571,1496,1358, 1263,1234,1114,1051, 1026,933,901,763,731,689.

Example 19

Dioxomolybdenum(VI) Bis(N,N-Dibutyl-2-Oxocyclopentane Carboxamidate)

3.26 g Dioxomolybdenum(VI) bis(acetylacetonate) and 5.02 g N,N-dibutyl-2-oxocyclopentane carboxamide were reacted according to General Preparation Procedure A. The product consisted of 7.90 g of a yellow solid.

$^1$H-NMR(CDCl$_3$):δ0.9-1.0(2×t,6H,CH$_2$CH$_3$),1.25-1.4(m, 8H,CH$_2$CH$_3$),1.4-1.6(m,8H,CH$_2$CH$_2$CH$_3$),1.8-1.95(m,2H, CH$_2$$^{cy}$),2.15-2.55(m,10H,CH$_2$$^{cy}$),3.1-3.2(m,4H, NCH$_2$),3.35 (t,1H,CHCO),3.45-3.6(m,4H,NCH$_2$),5.5,5.7 and 5.8(3×s, 2H,enol-CH).

FT-IR:2955,2871,1739,1632,1587,1562,1516,1456,1371, 1265,1230,1104,1026, 932,903,796,734,699,668.

Example 20

Dioxomolybdenum(VI) Bis(N,N-Bis-Dibutyl-2-Oxocyclopentane Carboxamidate) in TEGDME 3.29 Dioxomolybdenum(VI) bis(acetylacetonate) and 5.10 g N,N-dibutyl-2-oxocyclopentane carboxamide were reacted in 8.78 g TEGDME according to General Preparation Procedure C. The product consisted of 17.17 g of an orange brown solution in which crystals formed as the solution was left to stand.

Example 21

Dioxomolybdenum(VI) Acetylacetonate (N,N-Diethyl-3-Oxobutanamidate)

4.24 g Dioxomolybdenum(VI) bis(acetylacetonate) and 2.12 g N,N-diethyl-3-oxobutane amide were reacted according to General Preparation Procedure A. The product consisted of 4.95 g of a yellow, microcrystalline solid. $^1$H-NMR (DMSO-d$_6$):δ0.9and 1.1(2×t,12H,Me),1.9,2.0and 2.15(3×s, 9H,MeCO), 3.1-3.4(m,4H,CH$_2$N),5.45-6.0(6×s,2H,enol-CH).
FT-IR:2976,2934,1715,1588,1504,1437,1357,1308,1265, 1197,1080,1017,963, 931,904,783,666.

Example 22

Dioxomolybdenum(VI) (N,N-Diethyl-3-Oxobutanamidate) (N,N-Bis(2-Methoxyethyl)-3-Oxobutanamidate))

3.35 g Dioxomolybdenum(VI) bis(acetylacetonate) and a combination of 1.71 g N,N-diethyl-3-oxobutane amide and 2.35 g N,N-bis(2-methoxyethyl)-3-oxobutane amide were reacted according to General Preparation Procedure A. The product consisted of 5.42 g of a reddish, highly viscous oil.
$^1$H-NMR(DMSO-d$_6$):δ0.95-1.0(dt,6H,Me),1.05-1.15(m, 6H,Me),1.9-2.5(3×s,6H,MeCO),3.2-3.6(m,12H,CH$_2$N and CH$_2$O),5.5(dd,2H,enol-CH),5.9(d,1H,enol-CH).
FT-IR:2980,2889,1718,1587,1499,1453,1436,1355,1305, 1275,1195,1112,1013, 960,925,897,773,658.

Single-component polyurethane compositions

Examples 23 to 26 and Comparative Examples V1 to V2

For each example, the polyurethane polymer P1, whose preparation is described below, was mixed in a polypropylene beaker with screw cap by means of a centrifugal mixer (SpeedMixer™ DAC 150, FlackTek Inc.; 1 min at 2500 rpm) with a catalyst to form a homogeneous composition, and the composition so obtained was filled into an internally painted aluminum tube and this tube was closed in an airtight manner.

The polyurethane polymer P1 was prepared as follows:
1300 g Polyoxypropylenediol (Acclaim® 4200 N, from Bayer; OH number 28.5 mg KOH/g), 2600 g polyoxypropylene polyoxyethylenetriol (Caradol® MD34-02, from Shell; OH number 35.0 mg KOH/g), 600 g 4,4'-methylene diphenyl diisocyanate (4,4'-MDI; Desmodure® 44 MC L, from Bayer) and 500 g diisodecyl phthalate (DIDP; Palatinol® Z, from BASF) were reacted according to known methods at 80° C. to form an NCO-terminated polyurethane polymer with a content of free isocyanate groups of 2.05 wt %.

The resulting compositions were tested to determine their storage stability as well as their curing rate.

As a measurement of the storage stability, the change in the viscosity during storage with exposure to heat was determined. For this purpose, the compositions were stored in the closed tube in the oven at 60° C. and the viscosity at 20° C. was measured the first time after 4 hours (="viscosity fresh") and a second time after 7 days (="viscosity stored") storage duration. The storage stability is determined as the percent increase of the second viscosity value compared to the first one. For this purpose, the viscosity increase in % was calculated according to the following formula:

[(Viscosity after 7 d/viscosity after 4 h)−1]×100%.

As a measurement for the curing rate, the tack-free time (skin formation time [HBZ]) was determined, in particular for the compositions which had been stored for 4 hours at 60° C. (="HBZ fresh") and for the compositions which had been stored for 7 days at 60° C. (="HBZ stored"). For this purpose, the room-temperature compositions were applied in a layer thickness of approximately 3 mm to cardboard, and, under standard atmospheric conditions ("NK;" 23±1° C., 50±5% relative humidity), the time was determined in each case until the first time that no residues remained on the pipette after slightly tapping the surface of composition with a pipette made of LDPE.

The results of these tests are listed in Table 1.

TABLE 1

| Single-component polyurethane compositions (Quantities in parts by weight). | | | | | | |
|---|---|---|---|---|---|---|
| Example | 23 | 24 | 25 | 26 | V1 | V2 |
| Polyurethane polymer P1 | 50 | 50 | 50 | 50 | 50 | 50 |
| Catalyst Example 2 | 0.72 | — | — | — | — | — |
| Catalyst Example 5 | — | 0.78 | — | — | — | — |
| Catalyst Example 10 | — | — | 0.30 | — | — | — |
| Catalyst Example 20 | — | — | — | 0.77 | — | — |
| MoO$_2$(acac)$_2$$^a$ | — | — | — | — | 0.73 | — |
| Molybdenum carboxylate$^b$ | — | — | — | — | — | 0.29 |
| mmol-equiv./100 g$^c$ | 0.9 | 0.9 | 0.9 | 0.9 | 0.9 | 0.9 |
| Viscosity fresh (Pa · s) | 57.7 | 57.3 | 81.6 | 59.7 | 122 | 64.7 |
| Viscosity stored (Pa · s) | 98.0 | 87.1 | 111 | 104 | gelled | 84.6 |
| Viscosity increase (%) | 70 | 52 | 36 | 74 | >300 | 31 |
| HBZ fresh (min) | 86 | 94 | 145 | 95 | 83 | >360 |
| HBZ stored (min) | 150 | 154 | 170 | 110 | — | >360 |

$^a$20% solution in methyl ethyl ketone.
$^b$Molybdenum-2-ethyl hexanoate (15% Mo, from Shepherd).
$^c$mmol-equivalents of molybdenum atoms of the catalyst per 100 g of the composition.

It is evident from Table 1 that the single-component polyurethane compositions with the catalysts according to the invention have comparatively satisfactory storage stabilities and skin formation times.

Two-component polyurethane compositions

Examples 27 to 28 and Comparative Examples V3 to V7

For the preparation of the first component, for each example, a polyethertriol (Voranol® CP 4755, from Dow) and a catalyst according to Table 2 were intimately mixed in a centrifugal mixer (SpeedMixer™ DAC 150, FlackTek Inc.) for 30 s at 3000 rpm. A portion of the freshly prepared first component was subsequently filled into an internally painted aluminum tube; this tube was closed in an airtight manner and stored for 7 days in a convection oven at 60° C.

For each example, the rest of the freshly prepared first component was mixed in the described manner with a modified diphenylmethane diisocyanate (Desmodur® CD-L, produced by Bayer), which is liquid at room temperature, as second component according to Table 2 to form a polyurethane composition.

Likewise, for each example, the first component which had been stored for 7 days at 60° C. was mixed with the second component according to Table 2 in the same manner to form a polyurethane composition.

TABLE 2

Two-component polyurethane compositions
(Quantities in parts by weight).

| Example | 27 | 28 | V3 | V4 | V5 | V6 | V7 |
|---|---|---|---|---|---|---|---|
| First component: | | | | | | | |
| Voranol ® CP 4755 | 50 | 50 | 50 | 50 | 50 | 50 | 50 |
| Catalyst Example 2 | 0.71 | — | — | — | — | — | — |
| Catalyst Example 11 | — | 0.75 | — | — | — | — | — |
| $MoO_2(acac)_2$[a] | — | — | 1.74 | — | — | — | — |
| Molybdenum carboxylate[b] | — | — | — | 0.81 | — | — | — |
| DBTDL[c] | — | — | — | — | 0.46 | — | — |
| Coscat ® 83[d] | — | — | — | — | — | 0.02 | — |
| DABCO 33-LV ®[e] | — | — | — | — | — | — | 0.10 |
| mmol-equiv./100 g[f] | 0.80 | 0.86 | 2.68 | 2.27 | 0.13 | 0.03 | 1.07 |
| Second component: | | | | | | | |
| Desmodur ® CD-L | 5.10 | 5.10 | 5.10 | 5.10 | 5.10 | 5.10 | 5.10 |

[a]28.6% suspension in methyl ethyl ketone.
[b]Molybdenum-2-ethylhexanoate (15% Mo, from Shepherd).
[c]10% solution of dibutyltin dilaurate in diisodecyl phthalate.
[d]Bismuth tris(neodecanoate) in neodecanoic acid (16% Bi, from Erbslöh).
[e]33% solution of 1,4-diazabicyclo[2.2.2]octane in dipropylene glycol (from Air Products).
[f]mmol equivalents of metal atoms or amino groups of the catalyst per 100 g of the composition.

The polyurethane compositions were checked to determine the appearance, tack-free time, bubble formation and Shore A hardness, in particular in each case both for the composition with the freshly prepared first component and also for the composition with the first component which had been stored for 7 days at 60° C. Moreover, exclusively for the composition with the freshly prepared first component, the mechanical properties were also measured in the tensile test, in particular before and after various storage procedures for accelerated aging of the samples.

The appearance of the composition was evaluated purely visually and ranked as "clear," "turbid" or "inhomogeneous" ("inh.").

The tack-free time (skin formation time) was measured as described in Example 23.

The bubble formation was evaluated visually using the number ("many," "some," "none") of gas bubbles which occurred in the composition prepared for the determination of the skin formation time during its curing.

The Shore A hardness was determined according to DIN 53505 on test specimens that had been cured for 7 days under standard atmospheric conditions.

For the determination of the mechanical properties in the tensile test, films having a thickness of approximately 3 mm were prepared from the compositions, by pouring the composition into a flat PTFE mold and curing it for 7 days under standard atmospheric conditions. Tack-free, elastic films were obtained. From the films, dumbbell shaped samples were punched, having a length of 75 mm, with a bar length of 30 mm, and a bar width of 4 mm, and some of them were tested according to DIN EN 53504 at a traction rate of 200 mm/min to determine the tensile strength, the elongation at rupture, and the E modulus (at an elongation of 0.5 to 5.0%). The rest of the dumbbells were stored for 1 day at 100° C. in the convection oven, for example, for 10 days under "cataplasm" (40° C. and 100% relative humidity) or for 10 days under "cataplasm" as well as for 1 day at 100° C., whereafter, in each case, they were kept for one day under standard atmospheric conditions and tested as described according to DIN EN 53504.

The results of these tests are listed in Table 3.

TABLE 3

Properties of the two-component polyurethane compositions

| Example | 27 | 28 | V3 | V4 | V5 | V6 | V7 |
|---|---|---|---|---|---|---|---|
| Composition with freshly prepared first component: | | | | | | | |
| Appearance | clear | clear | inh. | clear | clear | clear | clear |
| Skin formation time (min) | 9 | 15 | 35 | 110 | 10 | 3 | 15 |
| Shore A hardness | 42 | 42 | 16 | 25 | 48 | 44 | 33 |
| Bubble formation | none | none | none | some | some | none | some |
| Tensile strength (MPa): 7 d/NK | 0.86 | 0.76 | 0.54 | 0.66 | 0.76 | 0.54 | 0.90 |
| +10 d/cataplasm | 0.75 | 0.80 | 0.62 | 0.71 | 0.71 | 0.79 | 0.82 |
| +1 d/100° C. | 0.92 | 0.82 | 0.66 | 0.68 | 0.60 | 0.73 | 0.86 |
| +10 d/cataplasm + 1 d/100° C. | 0.85 | 0.86 | 0.61 | 0.77 | 0.65 | 0.73 | 0.89 |
| Elongation at rupture (%): 7 d/NK | 78 | 67 | 81 | 83 | 65 | 42 | 100 |
| +10 d/cataplasm | 63 | 72 | 105 | 85 | 56 | 73 | 85 |
| +1 d/100° C. | 90 | 91 | 123 | 108 | 168 | 72 | 105 |
| +10 d/cataplasm + 1 d/100° C. | 83 | 97 | 110 | 124 | 170 | 74 | 108 |
| E modulus (MPa): 7 d/NK | 1.66 | 1.58 | 0.85 | 1.21 | 1.68 | 1.46 | 1.44 |
| +10 d/cataplasm | 1.66 | 1.57 | 0.85 | 1.21 | 1.68 | 1.56 | 1.47 |
| +1 d/100° C. | 1.57 | 1.36 | 0.92 | 1.00 | 0.60 | 1.49 | 1.23 |
| +10 d/cataplasm + 1 d/100° C. | 1.50 | 1.36 | 0.80 | 1.06 | 0.71 | 1.41 | 1.23 |
| Composition with stored | | | | | | | |
| Appearance | clear | clear | inh. | clear | clear | clear | clear |
| Skin formation time (min) | 9 | 15 | 30 | 120 | 10 | 45 | 15 |
| Shore A hardness | 44 | 46 | 32 | 34 | 48 | 45 | 32 |
| Bubble formation | none | none | none | some | some | some | some |

From Table 3 it is evident that the two-component polyurethane compositions with the catalysts according to the invention represent clear, homogeneous mixtures which have both before and also after storage comparatively short skin formation times and which cure without bubbles to form a material with comparatively high strength and satisfactory resistance.

Examples 29 to 30 and Comparative Examples V8 to V12

For the preparation of the first component, for each example, a polyether triol (Voranol®CP 4755, from Dow), a polyether diol (Acclaim® 4200, from Bayer), and a catalyst according to Table 4 were intimately mixed in a centrifugal mixer (SpeedMixer™ DAC 150, FlackTek Inc.) for 30 s at 3000 rpm. A portion of the freshly prepared first component was then filled into an internally painted aluminum tube; this tube was closed in an airtight manner, and stored for 7 days in a convection oven at 60° C.

For each example, the rest of the freshly prepared first component was mixed in the described manner with a modified diphenylmethane diisocyanate (Desmodur® CD-L, from Bayer), which is liquid at room temperature, as second component according to Table 4 to form a polyurethane composition.

Likewise, for each example, the first component which had been stored for 7 days at 60° C. was mixed with the second component according to Table 4 in the same manner to form a polyurethane composition.

The polyurethane compositions were checked as for Example 27 to determine the appearance, tack-free time, bubble formation and Shore A hardness, in particular in each case both for the composition with the freshly prepared first component and also for the composition with the first component which had been stored for 7 days at 60° C. Moreover, as described in Example 27, exclusively for the composition with the freshly prepared first component, the mechanical properties were also measured in the tensile test, in particular before and after various storage procedures for accelerated aging of the samples.

The results of these tests are listed in Table 5.

TABLE 5

Properties of the two-component polyurethane compositions

| Example | 29 | 30 | V8 | V9 | V10 | V11 | V12 |
|---|---|---|---|---|---|---|---|
| Composition with freshly prepared first component: | | | | | | | |
| Appearance | clear | clear | inh. | clear | clear | clear | clear |
| Skin formation time (min) | 15 | 35 | 17 | 105 | 27 | 90 | 35 |
| Shore A hardness | 44 | 41 | 42 | 32 | 48 | 42 | 33 |
| Bubble formation | none | none | none | some | many | none | many |
| Tensile strength (MPa): 7 d/NK | 0.75 | 0.72 | 0.77 | 0.63 | 0.77 | 0.71 | 0.65 |
| +10 d/cataplasm | 0.73 | 0.71 | 0.77 | 0.59 | 0.77 | 0.73 | 0.66 |
| +1 d/100° C. | 0.77 | 0.75 | 0.76 | 0.62 | 0.48 | 0.70 | 0.72 |
| +10 d/cataplasm + 1 d/100° C. | 0.75 | 0.72 | 0.87 | 0.66 | 0.52 | 0.74 | 0.69 |
| Elongation at rupture (%): 7 d/NK | 97 | 117 | 115 | 109 | 105 | 124 | 135 |
| +10 d/cataplasm | 95 | 125 | 116 | 112 | 105 | 119 | 148 |
| +1 d/100° C. | 136 | 188 | 148 | 181 | 341 | 137 | 193 |
| +10 d/cataplasm + 1 d/100° C. | 122 | 139 | 171 | 156 | 303 | 178 | 181 |
| E modulus (MPa): 7 d/NK | 1.42 | 0.99 | 1.12 | 0.89 | 1.20 | 0.82 | 0.88 |
| +10 d/cataplasm | 1.18 | 0.94 | 1.06 | 0.84 | 1.30 | 0.98 | 0.81 |
| +1 d/100° C. | 1.01 | 0.76 | 0.98 | 0.61 | 0.20 | 0.91 | 0.69 |
| +10 d/cataplasm + 1 d/100° C. | 1.08 | 0.96 | 1.04 | 0.82 | 0.28 | 0.80 | 0.65 |
| Composition with stored first component: | | | | | | | |
| Appearance | clear | clear | inh. | clear | clear | clear | clear |
| Skin formation time (min.) | 8 | 30 | 14 | 100 | 27 | 300 | 35 |

TABLE 4

Two-component polyurethrane compositions (Quantities in parts by weight).

| Example | 29 | 30 | V8 | V9 | V10 | V11 | V12 |
|---|---|---|---|---|---|---|---|
| First component: | | | | | | | |
| Voranol ® CP 4755 | 33.3 | 33.3 | 33.3 | 33.3 | 33.3 | 33.3 | 33.3 |
| Acclaim ® 4200 | 16.7 | 16.7 | 16.7 | 16.7 | 16.7 | 16.7 | 16.7 |
| Catalyst Example 2 | 0.71 | — | — | — | — | — | — |
| Catalyst Example 11 | — | 0.48 | — | — | — | — | — |
| MoO$_2$(acac)$_2$[a] | — | — | 1.64 | — | — | — | — |
| Molybdenum carboxylate[b] | — | — | — | 0.70 | — | — | — |
| DBTDL[c] | — | — | — | — | 0.49 | — | — |
| Coscat ® 83[d] | — | — | — | — | — | 0.02 | — |
| DABCO 33-LV ®[e] | — | — | — | — | — | — | 0.14 |
| mmol-equiv./100 g[f] | 0.81 | 0.55 | 2.54 | 1.96 | 0.14 | 0.03 | 1.50 |
| Second component: | | | | | | | |
| Desmodur ® CD-L | 5.00 | 5.00 | 5.00 | 5.00 | 5.00 | 5.00 | 5.00 |

[a]28.6% suspension in methyl ethyl ketone.
[b]Molybdenum-2-ethylhexanoate (15.5% Mo, from Shepherd).
[c]10% solution of dibutyltin dilaurate in diisodecyl phthalate.
[d]Bismuth tris(neodecanoate) in neodecanoic acid (16% Bi, from Erbslöh).
[e]33% solution of 1,4-diazabicyclo[2.2.2]octane in dipropylene glycol (from Air Products).
[f]mmol equivalents of metal atoms or amino groups of the catalyst per 100 g of the composition.

TABLE 5-continued

Properties of the two-component polyurethane compositions

| Example | 29 | 30 | V8 | V9 | V10 | V11 | V12 |
|---|---|---|---|---|---|---|---|
| Shore A hardness | 45 | 44 | 45 | 40 | 45 | 41 | 40 |
| Bubble formation | none | none | none | some | some | some | some |

From Table 5 it is evident that the two-component polyurethane compositions with the catalysts according to the invention represent clear, homogeneous mixtures which have both before and also after storage comparatively short skin formation times and which cure without bubbles to form a material with comparatively high strength and satisfactory resistance.

Examples 31 to 39

As described for Example 27, for the preparation of the first component, in each case, a polyether triol (Voranol® CP 4755, from Dow) and a catalyst according to Table 6 were mixed. A portion of the freshly prepared first component was then filled into an internally painted aluminum tube; this tube was closed in an airtight manner and stored for 7 days in a convection oven at 60° C.

The rest of the freshly prepared first component was mixed for each example in the manner described for Example 27 with a modified diphenylmethane diisocyanate (Desmodur CD-L, from Bayer), which is liquid at room temperature, as second component according to Table 6 to form a polyurethane mixture.

Likewise, for each example, the first component which had been stored for 7 days at 60° C. was mixed with the second component according to Table 6 in the same manner to form a polyurethane composition.

The polyurethane compositions were checked as for Example 27 to determine the appearance, tack-free time, bubble formation and Shore A hardness as well as the mechanical properties in the tensile test.

The results of these tests are listed in Table 7.

TABLE 6

Two-component polyurethane compositions

| Example | 31 | 32 | 33 | 34 | 35 | 36 | 37 | 38 | 39 |
|---|---|---|---|---|---|---|---|---|---|
| First component: | | | | | | | | | |
| Voranol ® CP 4755 | 30 | 30 | 30 | 30 | 30 | 30 | 30 | 30 | 30 |
| Catalyst Example 2 | 1.13 | 0.16 | — | — | — | — | — | — | — |
| Catalyst Example 5 | — | — | 1.22 | — | — | — | — | — | — |
| Catalyst Example 7 | — | — | — | 1.28 | — | — | — | — | — |
| Catalyst Example 10 | — | — | — | — | 0.46 | — | — | — | — |
| Catalyst Example 11 | — | — | — | — | — | 1.10 | — | — | — |
| Catalyst Example 14 | — | — | — | — | — | — | 0.39 | — | — |
| Catalyst Example 17 | — | — | — | — | — | — | — | 1.12 | — |
| Catalyst Example 22 | — | — | — | — | — | — | — | — | 0.35 |
| mmol-equiv./100 g$^a$ | 2.09 | 0.30 | 2.06 | 2.06 | 2.06 | 2.06 | 1.99 | 2.06 | 1.98 |
| Second component: | | | | | | | | | |
| Desmodur ® CD-L | 3.10 | 3.10 | 3.10 | 3.10 | 3.10 | 3.10 | 3.10 | 3.10 | 3.10 |

$^a$mmol-equivalents of molybdenum atoms of the catalysts per 100 g of the composition.

TABLE 7

Properties of the two-component polyurethane compositions.

| Example | 31 | 32 | 33 | 34 | 35 | 36 | 37 | 38 | 39 |
|---|---|---|---|---|---|---|---|---|---|
| Composition with fresh prepared first component: | | | | | | | | | |
| Appearance | clear | clear | clear | clear | clear | clear | clear | clear | clear |
| Skin formation time (min) | 11 | 40 | 4 | 10 | 8 | 9 | 7 | 12 | 11 |
| Shore A hardness | 32 | 39 | 44 | 44 | 45 | 42 | 48 | 46 | 45 |
| Bubble formation | none | none | none | none | none | none | none | none | none |
| Composition with stored first component: | | | | | | | | | |
| Appearance | clear | clear | clear | clear | clear | clear | clear | clear | clear |
| Skin formation time (min) | 7 | 31 | 5 | 5 | 3 | 8 | 6 | 6 | 2 |
| Shore A hardness | 39 | 40 | 46 | 44 | 48 | 47 | 46 | 46 | 44 |
| Bubble formation | none | none | none | none | none | some | none | none | none |

As can be seen in Table 7, the two-component polyurethane compositions with the catalysts according to the invention represent clear, homogeneous mixtures which have relatively short skin formation times both before and after storage and which cure largely without bubbles to form a material with a satisfactory Shore A hardness.

The invention claimed is:

1. A curable composition comprising (1) at least one curable component selected from the group consisting of an epoxy resin, an acrylate and a silicone, and (2) at least one dioxomolybdenum(VI) complex compound of formula $MoO_2(L)_x(Y)_{2-x}$, where x stands for 1 or 2, Y for a ligand with a single negative charge, and L for a ligand of formula (I),

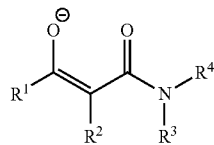

where $R^1$ and $R^2$ independently of one another stand for a hydrogen residue, for a monovalent saturated or unsaturated hydrocarbon residue having 1 to 10 carbon atoms, or together stand for a bivalent alkylene residue having 3 to 6 carbon atoms, and $R^3$ and $R^4$ independently of one another stand for a hydrogen residue, a monovalent saturated hydrocarbon residue, which optionally contains heteroatoms, having 1 to 12 carbon atoms, or together stand for a bivalent alkylene residue, which optionally contains heteroatoms, having 3 to 6 carbon atoms, wherein said dioxomolybdenum(VI) complex compound is present in an amount sufficient to catalyze the curing of said curable component.

2. The curable composition according to claim 1, wherein the component comprises an epoxy resin.

3. The curable composition according to claim 1, wherein the component comprises an acrylate.

4. The curable composition according to claim 1, wherein the component comprises a silicone.

5. The curable composition according to claim 1, wherein x stands for 2.

6. The curable composition according to claim 1, wherein x stands for 1.

7. The curable composition according to claim 6, wherein Y is a carbonylate.

8. The curable composition according to claim 7, wherein the carbonylate is 1,3-dicarbonylate.

9. The curable composition according to claim 8, wherein the 1,3-dicarbonylate is acetylacetonate or 2,2,6,6,-tetramethylheptane-3-5,dionate.

* * * * *